US007241570B2

(12) United States Patent
Prescott et al.

(10) Patent No.: US 7,241,570 B2
(45) Date of Patent: Jul. 10, 2007

(54) METHOD OF SCREENING FOR AGENTS THAT REGULATE THE SHEDDING OF MEMBRANE BOUND PROTEINS AND METHODS OF USE

(75) Inventors: Stephen M. Prescott, Salt Lake City, UT (US); Matthew Topham, Salt Lake City, UT (US); Fumio Sakane, Sapporo (JP); Akinobu Taketomi, Nakatsu (JP)

(73) Assignee: University of Utah Research Foundation, Salt Lake City, UT (US)

( * ) Notice: Subject to any disclaimer, the term of this patent is extended or adjusted under 35 U.S.C. 154(b) by 217 days.

(21) Appl. No.: 10/471,122

(22) PCT Filed: Mar. 22, 2002

(86) PCT No.: PCT/US02/08854

§ 371 (c)(1),
(2), (4) Date: Sep. 8, 2003

(87) PCT Pub. No.: WO02/077178

PCT Pub. Date: Oct. 3, 2002

(65) Prior Publication Data

US 2004/0110178 A1 Jun. 10, 2004

Related U.S. Application Data

(60) Provisional application No. 60/278,158, filed on Mar. 23, 2001.

(51) Int. Cl.
*C12Q 1/48* (2006.01)
*C12Q 1/68* (2006.01)

(52) U.S. Cl. .......................................... 435/6; 435/15

(58) Field of Classification Search ................. 435/15, 435/6, 194
See application file for complete search history.

(56) References Cited

OTHER PUBLICATIONS

Sakane et al., J.B.C., 271(14), 8394-8401, 1996.*
Zhao, Jinsong, "Pulmonary Hypoplasia in Mice Lacking Tumor Necrosis Factor-α Converting Enzyme Indicates an Indispensable Role for Cell Surface Protein Shedding during Embryonic Lung Branching Morphogensis." Development Biology, 232, 204-218 (2001).

* cited by examiner

*Primary Examiner*—Maryam Monshipouri
(74) *Attorney, Agent, or Firm*—Madison & Austin

(57) ABSTRACT

The present invention provides a method of screening for agents which may regulate or inhibit the activities of TACE and TGF-α. These agents may act by enhancing or inhibiting the activity of DGK-δ. An activity of DGK-δ is the enzymatic conversion of DAG to PA. The method includes contacting a cell or organism with a test agent determining the activity of DGK-δ within the cell. An agent with reduces or increases the activity of DGK may be used to regulate or inhibit the activity of TACE and TGF-α. Such agents can be used to treat diseases such as cancer where cell growth and division and inflamation are important factors.

14 Claims, 4 Drawing Sheets

METHOD OF SCREENING FOR AGENTS THAT REGULATE THE SHEDDING OF MEMBRANE BOUND PROTEINS AND METHODS OF USE

This application is the National Phase entry of International Application PCT/US02/08854, filed Mar. 22, 2002, which claims priority to U.S. Provisional Application 60/278,158, filed Mar. 23, 2001.

FIELD OF THE INVENTION

The present invention relates to agents that regulate the shedding of membrane bound proteins. More specifically, the invention relates to screening assays for agents which can be used to increase or decrease the level of shedding of membrane bound protein, and novel methods of regulating cell growth and division and inflamation which involve the administration of agents discovered using the assays.

TECHNICAL BACKGROUND

Cancer is a disease in which normal body cells are changed, becoming able to multiply without regard to normal cellular restraints and to invade and colonize areas of the body normally occupied by other cells. See B. Alberts et al., *Molecular Biology of the Cell* 1255-1294 (3d ed. 1994). According to the American Cancer Society, one-half of all American men and one-third of all American women will at some point in their lives develop cancer.

Due to the ability of cancer cells to spread and rapidly proliferate, it is difficult to treat cancer patients by attempting to selectively kill cancerous cells. Some have compared the difficulty of this task to the difficulty of completely ridding a garden of weeds. As with weeds, if only a few cancer cells are left untouched by treatment, they may again spread throughout the body, causing a recurrence of the disease. See id. at 1267. Current treatments for cancer include surgery and therapies using chemicals and radiation. The effectiveness of these treatments is often limited, however, since cancer cells that have spread from the original tumor site may be missed by surgery and radiation, and since chemical treatments which kill or disable cancer cells are often capable of causing similar damage to normal cells. See id.

Hope for better treatments for cancer focuses on obtaining a better understanding of carcinogenesis—the series of events which transforms a normal cell into a cancer cell. It is hoped that such an understanding will help researchers and physicians direct treatments solely toward cancer cells or their precursors, thus preventing or treating cancer and avoiding damage to healthy body tissues. As more data is gathered on the transformation of a normal cell into a cancer cell, it is apparent that a number of genes and proteins can play a role in carcinogenisis. Additionally, there are many proteins whose activity has not been fully determined and that may play a role in carcinogenesis.

Diacylglycerol kinase (DGK) belong to one family of enzymes that are not completely understood. DGKs catalyze the phosphorylation of diacylglycerol (DAG) to produce phosphatidic acid (PA). Sakane, F. & Kanoh, *Int J Biochem Cell Biol* 29, 1139-1143 (1997); Topham, M. K. & Prescott, S. M. *J Biol Chem* 274, 11447-50 (1999). Both the substrate (DAG) and the product (PA) of the DGK reaction are key factors in intracellular signaling. For example, DAG activates protein kinase Cs (PKC) and some guanine nucleotide exchange factors such as RasGRP. Nishizuka, Y. *Science* 233, 305-312 (1986).; Ebinu, J. O. et al. *Science* 280, 1082 (1998). The consumption of DAG by DGKs is thought to attenuate these actions, so DGKs are thought to terminate the activity of PKCs and other DAG-activated proteins. Conversely, by generating phosphatidic acid, DGKs may initiate a variety of cellular events. For example, PA has been reported to modulate a typical PKC isoforms, Ras-GAP, phosphatidylinositol (PI) 5-kinases (Moritz et al., 1992) and other signaling proteins, and PA is mitogen for a variety of cells. Exton, J. H. *Physiological Reviews* 77, 303 (1997).

It is unclear which functions attributable to DAG and PA reflect the actions of DGK, since phospholipase D (PLD) also releases PA, and DAG is also produced by PA phosphatase. Sakane, F. & Kanoh, *Int J Biochem Cell Biol* 29, 1139-1143 (1997); Topham, M. K. & Prescott, S. M. *J Biol Chem* 274, 11447-50 (1999). Exton, J. H. *Physiological Reviews* 77, 303 (1997). It is likely, however, that signaling lipids derived from each pathway—the PLC/DGK or PLD/PA phosphatase—have distinct functions by virtue of the parent lipids for each reaction. Hodgkin, M. N. et al. *Trends Biochem Sci* 23, 200-(1998). For example, the predominant substrate of PLD is phosphatidylcholine, which is composed primarily of saturated fatty acids, so the reaction product, phosphatidic acid, is also composed mostly of saturated fatty acids. Alternatively, DGKs are thought to phosphorylate DAG generated by phosphatidylinositol—specific phospholipase Cs. Since phosphatidylinositols are enriched in unsaturated fatty acids, DAG derived from this reaction is predominantly unsaturated, so the PA generated by DGK activity is composed mostly of unsaturated fatty acids. Id. And, there is evidence that DAG and PA, depending on their lipid composition, can differentially activate protein targets. For example, unsaturated DAG is a more potent activator of protein kinase Cs than is saturated DAG, while saturated PA species induce MAPK activation to a greater extent that unsaturated PAs. Thus, DGKs and PLDs likely influence distinct signaling events.

While most attention on PA signaling has been focused on the PLD reaction, PA generated by DGKs likely has signaling functions as well. Flores and colleagues identified a potential role for DGK-generated PA in T lymphocyte proliferation. Flores, I., et al. *J Biol Chem* 271, 10334-10340 (1996). They noted that when T lymphocytes were treated with IL-2, a growth signal, DKGα translocated to the perinuclear space. Using DGK inhibitors, they presented evidence that the PA produced by this isozyme was necessary for progression to S phase of the cell cycle, suggesting that PA generated by DKGα in this context had a signaling role. Additionally, Cutrupi et al demonstrated that active DKGα was required for hepatocyte growth factor induced migration of endothelial cells. Cutrupi, S. et al. *EMBO J.* 19, 4614-4622 (2000). Their data suggested that generation of PA by DKGα was necessary for the migration, but they could not identity the protein target of the phosphatidic acid.

As mentioned above, there are many proteins whose activity can be influenced by PA, so DGKs could regulate a variety of cellular events that are dependent on PA. Diacylglycerol kinases can also influence proteins regulated by DAG. In this case, however, DGKs are likely inhibitory because they terminate DAG signaling. Indeed, DGKζ, and not other DGK isotypes, inhibited the activity of RasGRP, a Ras guanyl nucleotide exchange factor (GEF) whose activity requires DAG. Topham, M. K. & Prescott, S. M. *J. Cell Biol.* 152 (2001). And, Nurrish et al presented evidence that a *Caenorhabditis elegans* DGK negatively regulated synaptic transmission by metabolizing DAG that would otherwise activate Unc-13, a protein activated by DAG that participates in neurotransmitter secretion. Nurrish, S., et al. *Neuron* 24, 231-242 (1999). Thus, by virtue of their enzymatic activity, DGKs can influence signaling events mediated by both DAG and PA. As these lipids can affect many protein targets, diacylglycerol kinases occupy an interesting biologic niche.

The DGK family is large and diverse. As with other enzymes in signaling pathways, such as PKC and PI-specific phospholipase C, mammalian DGKs are a family whose isozymes differ in their structures, patterns of tissue expression and catalytic properties. Sakane, F. & Kanoh, *Int J Biochem Cell Biol* 29, 1139-1143 (1997); Topham, M. Y & Prescott, S. M. *J Biol Chem* 274, 11447-50 (1999). Nine mammalian DGK isoforms have been identified. All of them contain a catalytic domain that is necessary for kinase activity. The DGK catalytic domains likely function similarly to the C3 regions of PKCs by presenting ATP as the phosphate donor. In addition to these domains, all DGKs have at least two cysteine-rich regions homologous to the C1A and C1B motifs of PKCs. DGKθ has three. These domains in DGKs are thought to present diacylglycerol for phosphorylation, but this has not been conclusively demonstrated.

In addition to these motifs, most DGKs have other structural domains that likely perform regulatory roles and are used to group the DGKs into the five subfamilies. Type I DGKs have calcium-binding EF hand motifs, making these isoforms calcium responsive. Diacylglycerol kinases having PH domains at their amino termini are grouped as type II. No specific function has been identified for these domains, but the PH domain of DGKδ can bind phosphatidylinositols (PIs). DGKδ also has at its C-terminus a sterile alpha motif (SAM). Its function is unclear, but SAM domains can be sites of protein—protein interactions. DGKε is a type III enzyme, and although it does not have any identifiable regulatory domains, it strongly prefers an arachidonoyl group at the sn-2 position making it the only DGK that has specificity toward acyl chains of DAG. This preference suggests that DGKε may be a component of the PI cycle that accounts for the enrichment of PI species with arachidonate. Type IV DGKs have a region homologous to the phosphorylation site domain of the MARCKS protein, and at their C-termini, four ankyrin repeats. Finally, DGKθ is a type V enzyme with three cysteine-rich domains and a PH domain. Their structural diversity and distinct expression patterns suggest that each isoform may perform a different function.

While many DGK isoforms have been identified in mammals, one or only a few DGK isoforms have been identified in organisms such as *Caenorhabditis elegans, Drosophila melanogaster*, and *Arabidopsis thaliana*. Topham, M. K. & Prescott, S. M. *J Biol Chem* 274, 11447-50 (1999). Moreover, at present, no DGK gene has been identified in yeast. The number and distribution of mammalian DGKs suggest that they have roles in processes specific to higher vertebrates, such as development, advanced neural functions, immune surveillance, and tumorigenesis. To date, however, there have been few studies of the specific functions of individual DGK isoforms.

Understanding the DGKs occupy crucial positions in the regulation of cellular signaling agents, it would thus be an improvement in the art to characterize the function of a DGK isoform. Specifically it would be an improvement in the art to characterize the function of a mammalian DGKδ enzyme. It would be an additional advancement to provide methods of screening for agents that inhibit the activity of the DGKδ enzyme. It would be a further advancement if such agents could be used to inhibit cell growth or inflamation.

BRIEF SUMMARY OF THE INVENTION

The present invention relates to methods of screening for agents that could be used to treat disease in humans and other mammals. The diseases and conditions that can potentially be treated by therapeutic agents determined by the method of the present invention include cancer, inflamation, and Alzheimer's. The methods of the invention are based the discovery that DGKδ is an important enzyme in the activation of (TACE) in cells and subsequent release of membrane bound proteins such as TNFα, TGFα, β-APP, and L-selectin. Thus, agents that inhibit or enhance the activity of DGKδ have potential for regulating the expression of TNFα, TGFα, β-APP, and L-selectin. Likewise, other enzymes such as p75 TNF receptor, p55 TNF receptor, growth hormone binding protein, erbB4/Her4, interleukin-6 receptor alpha, and notch receptor are known substrates of TACE which may be regulated by agents that inhibit or enhance the activity of DGKδ. Other probable TACE which maybe regulated by agents that inhibit or enhance DGKδ activity are EGF, amphiregulin, betacellulin, epiregulin, heparin binding EGF (HB-EGF), and epigen.

The method of the present invention can be used to screen for agents that regulate TACE activity. Such regulatory agents may either increase or decrease the level of TACE activity in a cell or organism. To determine if a test agent has such regulatory properties a cell maybe contacted with a test agent. The cell generally may express or over-express DGKδ. After the cell has been contacted by the test agent, the level of DGKδ activity in the cell maybe determined. An agent that increases or decreases the activity of DGKδ in the cell may be used to regulate TACE activity.

Functional activity of DGKδ can be the enzymatic conversion of DAG to PA, the membrane release of TACE substrates, or epidermal growth factor receptor activation. A test agent may regulate TACE activity by enhancing or interfering with the binding of DAG to DGKδ. Alternatively, the activity of DGKδ maybe determined by the level of DGKδ present in the cell. The level mRNA encoding for DGKδ may also be used to determine whether the activity of DGKδ has been increased or decreased by the test compound.

The cells used to determine the potential of the test agent tor regulate TACE maybe any of a number of types of cells known in the art. For example, the cell maybe grown in a cell culture. Such cultured cells maybe cancer cells, Hep G2 cells, hepatocytes, fibroblast, just to name a few. Additionally, the cell may be a cell within a multicellular organism. For example a mammal such as a mouse can be used to test the ability of the test compound to regulate TACE.

The ability of a compound to regulate TACE activity may also be determined by a method that determines whether the test agent causes an increase or reduction in the level of a DGKδ gene product or DGKδ mRNA in a cell as compared to a control. A test compound that causes an increase or reduction the level of a DGKδ gene product or DGKδ mRNA maybe used to regulate the activity of TACE.

In other embodiments of the invention, a test compound can be screened for its potential to reduce extracelluar levels of TGFα. TGFα is a membrane bound protein which is released by the proteolytic activity of TACE. To determine whether a compound may reduce extra cellular levels of TGFα, a cell which expresses or over expresses DGKδ maybe contacted with a test agent. Then, the level of DGKδ activity in the cell is assessed. A test agent which reduces the activity of DGKδ shows a potential for reducing extra cellular levels of TGFα. One activity of DGKδ which may be affected by the test agent is the enzymatic conversion of DAG to PA. The agent may, for example, interfere with the binding of DAG to DGKδ. Cells used to screen agents may be those known in the art such as cell cultures or cells within a multicellular organism.

In yet other embodiments of the invention agents can be screened for the ability to regulate cell growth and division. The method includes contacting a cell or organism with a test agent and measuring the level measuring level of the DGKδ gene product or DGKδ mRNA expressed in the cell. An agent that reduces or increases the level DGKδ gene product or DGKδ mRNA may have potential as regulators of cell growth and division. The level of the DGKδ gene product or DKGδ mRNA may be measured by directly quantifying the protein or mRNA, or alternatively the levels may be measured by detecting the level of DKGδ activity in the cell. Such activity of DGKδ may be the conversion of DAG to PA.

A method of screening for agents that inhibit inflamation is also presented. The method includes contacting a cell or organism with a test agent. Such cells or organism having at least one copy of the DGKδ gene which expresses or overexpresses DGKδ. The level of DGKδ activity or DGKδ mRNA may be measured to determine whether the test agent decreases the level or activity of DKGδ. An agent that lowers the level or activity of DGKδ as compared to a wild-type or other control may have potential to regulate or inhibit inflammation.

From such screening methods, methods of regulating the activity of TACE, TGFα, cell growth and division, and inflamation may also be developed. The methods include the administering an effective amount of a compound that reduces or increases the activity DGKδ. The compound may be selected by the methods described herein.

DETAILED DESCRIPTION OF THE INVENTION

Figure 1:
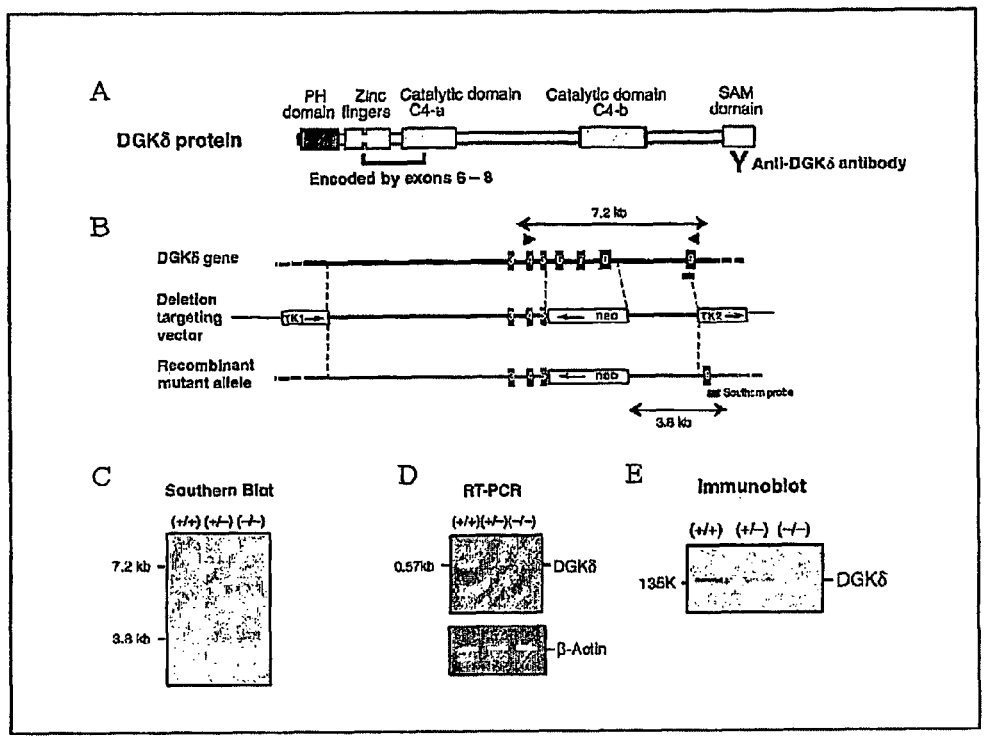
FIG. 1A is a schematic representation of the structural organization of DGKδ protein.
FIG. 1B is a schematic representation of the DGKδ gene, the targeting vector, and the recombinant mutant allele.
FIG. 1C is a photograph showing Southern blot analysis of tail DNA.
FIG. 1D is a photograph showing the expression of the DGKδ gene in primary embryonic fibroblasts.
FIG. 1E is a photograph showing the immunoblot detection of DKGδ in cell lysates.

The present invention relates to methods of screening for agents that could be used to treat disease in humans and other mammals. The diseases and conditions that can potentially be treated by therapeutic agents determined by the method of the present invention include cancer, inflamation, and Alzheimer's. The methods of the invention are based the discovery that DKGα is an important enzyme in the activation of (TACE) in cells and subsequent release of membrane bound proteins such as TNFα, TGFα, β-APP, and L-selectin TACE is responsible for the proteolytic shedding from cells of a diverse group of membrane-anchored proteins including L-selectin, TNFα, p75 TNFα receptor II, TGFα, and β-APP. Buxbaum, J. D., et al., *J. Biol. Chem.* 273, 27765-27767 (1998); Peschon, J. J., et al., *Science* 282, 1281-1284 (1998); Werb, Z., & Yan, Y., *Science* 282, 1279-1280 (1998). Other TACE substrates include p75 TNF receptor, p55 TNF receptor, growth hormone binding protein, erbB4/Her4, interleukin-6 receptor alpha, and notch receptor. Merlos-Suarez, A., et al., *J. Biol. Chem.* 276: 48510-48517 (2001); Zhang, Y., et al., *Endocrinology* 141: 4342-4348 (2000). EGF, amphiregulin, betacellulin, epireguun, heparin binding EGF (HB-EGF), and epigen may also be TACE substrates because TACE-deficient and EGFR-deficient mice are very similar, but single knockouts of the EGF receptor ligands have mild phenotypes and EGFR ligands are shed. Olayioye, M. A., et al. *EMBO Journal* 19:3159-3167 (2000); Strachan, L., et al., *J. Biol Chem* 276:18265-18271 (2001). Consequently, the activity of TACE may regulate a wide array of physiologic and pathologic functions such as leukocyte rolling and extravasation into sites of inflammation (L-selectin), inflammatory responses (TNFα and its receptor), cell growth and tumorigenesis (TGFα), and Alzheimer's disease (β-APP). Hooper, N. M., et al. *Biochem. J.* 321, 265-279 (1997); Werb, Z., & Yan, Y., *Science* 282, 1279-1280 (1998). Perhaps the most dramatic demonstration of the importance of TACE activity was by Peschon et al., who showed that a targeted mutation in TACE was lethal in mice and caused widespread epithelial cell organization and maturation defects. In addition to deficiency of TACE function in mutant mice, abnormally high activity of TACE can also have grave consequences. Overproduction of TGFα can initiate and accelerate tumorigenesis in vivo. Matsui, Y., et al., *Cell* 61, 1147-1155 (1990); Sandgren, E. P., et al., *Mol. Cell. Biol.* 13, 320-330 (1993). TACE activity, then, must be tightly regulated. At present, very little is known about how this occurs.

It has been reported that mature cell surface TACE is active in the basal state. Black, R. A., et al. *Nature* 385, 729-733 (1997). The requirement for a basal level of TACE activity for normal cell growth and development is shown by the phenotype of targeted mutant mice which exhibit dysmorphic epithelial development resulting in lethality. Peschon, J. J., et al., *Science* 282, 1281-1284 (1998). TACE activity must also be regulated under certain conditions, but the events enhancing its activity and the mechanism by which this occurs are poorly characterized. It is known that upregulated cell surface TACE activity does not require TACE transcription, translation, or mobilization to the cell surface, suggesting that either TACE enzymatic activity is directly affected, perhaps by a conformational change or that of TACE substrates become more easily accessible. Zhang, Z., et al., *J. Biol. Chem.* 275, 15839-15844 (2000).In vitro experiment shave indicated that several factors, including unspecified factors in serum, lipopolysaccharide, and phorbol esters appear to upregulate TACE activity. Buxbaum, J. D., et al., *Proc. Natl. Acad. Sci. USA* 91, 4489-4493 (1994); Merlos-Suarez, A., et al., *J. Biol. Chem.* 273, 24955-24962 (1998); Pandiella, A., & Massague, J., *J. Biol. Chem.* 266, 5769-5773 (1991). The mechanisms linking these molecules to stimulation off TACE activity are unclear, but may include activation of protein kinase C (PKC) isoforms by phorbol esters and generation of nitric oxide (NO), which may cause a conformational change in TACE through covalent modification.

It is shown herein that DGKδ is necessary for proper basal activity of TACE and for upregulation of its activity by exogenous serum or phorbol esters. Supporting this conclusion, the phenotype of mice null for DGKδ was almost identical to mice with a targeted mutation of TACE. Both types of knockout mice had stunted whiskers, open eyelids, and severely dysmorphic epithelial development in multiple organs. While the phenotype resulting from deletion of DGKδ might have resulted from altered signaling events downstream of EGF receptor activation, a process enabled by TACE activity, this was unlikely, since evidence was found that the EGFR signaling cascade was normal in fibroblasts isolated from the null mice. More likely, DGKδ affected TACE activity directly or altered a signaling event necessary for TACE function. Supporting this notion, reduced shedding of overexpressed TGFα and endogenous β-APP from the null fibroblasts was found compared to wild-type fibroblasts. Further, overexpression of DGKδ increased shedding of co-expressed TGFα. These data indicate that DGKδ is required for proper TACE function, but they do not distinguish whether DGKδ has a direct affecting TACE activity or whether it regulates an upstream event necessary for TACE activation.

It was observed that the two proteins co-localized in vesicles and co-immunoprecipitated. Moreover, their association was enhanced in the presence of either serum or PMA, suggesting that stimulation of TACE activity required that it physically associate with DGKδ. These data suggest that DGKδ activates TACE directly rather than affecting an upstream signaling event. Proximity of the two proteins may be essential for several reasons. Primarily, DGKδ may provide a factor necessary for TACE activity. As a lipid kinase, one obvious possibility would be through its production of phosphatidic acid (PA). It is not known whether PA directly activates TACE, but PA can dramatically stimulate the activity of several other proteins. Notably, phosphatidylinositol 5-kinases are 8-14 fold more active in the presence of PA, and this lipid is also an activator of NADPH oxidase in leukocytes. Ishihara, B., et al., *J. Biol. Chem.* 273, 8741-8748 (1998); Babior, B. M., *Blood* 93, 1464-1476 (1999). Phosphatidic acid can also participate in recruitment of cytosolic proteins to the membrane. For example, maximal translocation of Raf-1 to the membrane requires PA. Rizzo, M. A., et al., *J. Biol. Chem.* 275, 23911-23918 (2000). Through PA production, therefore, DGKδ may participate in recruiting proteins necessary for TACE activity or by facilitating presentation of its substrates. Alternatively, since phosphatidic acid may participate in formation of vesicles and their fusion with the membrane, PA produced by DGKδ may increase cell surface expression of TACE by facilitating fusion of vesicles containing TACE with the surface membrane. Roth, M. G. & Stemweis, P. C., *Curr. Opin. Cell Biol.* 9, 519-526 (1997). This mechanism is less likely because a difference in transferrin-stained vesicles was not detected between wild-type and DGKδ-null murine fibroblasts. However, subtle effects that were not morphologically apparent cannot be excluded.

DGKδ activity must be precisely regulated, as reduced expression in mutants results in dysmorphic epithelial development and abnormally high DGKδ activity may activate the EGF receptor through stimulation of TACE activity. Growth and migration of epithelial tumor cell lines is partly dependent on an autocrine activation loop regulating the EGF receptor. Ziober, B. L., et al. *J. Biol. Chem.* 268, 691-698 (1993). As such, overexpression of DGKδ and through it, TACE, may lead to unchecked cell growth and possibly to tumorigenesis. Increased DGKδ mRNA in tumor tissue from liver and from several tumor cell lines derived from both liver and lung was found, suggesting that, indeed, high DGKδ activity may be associated with transformation of cells. If, in some cases, abnormally high DGKδ activity contributes to cell transformation, it may be possible to attenuate cell growth by reducing DGKδ activity. Unfortunately, very little is known about how the activity of DGKδ is regulated. It was observed that classical PKC isoforms can phosphorylate the PH domain of DGKδ in vitro (not shown), but the consequences of this modification are not clear. Though modification does not appear to alter DGKδ kinase activity, it may affect DGKδ interaction with membrane phosphatidylinositols or other proteins. Phosphorylation of DGKδ by PKC isoforms is of interest because PMA, which increases TACE-mediated shedding, also activates many PKC isoforms, which have been implicated as activators of TACE. The role that PKC activity has in activating TACE is unclear, but based on experiments, it may involve phosphorylation of DGKδ. Alternatively, PMA may directly activate DGKδ by binding to its C 1 domains. Ron, D. & Kazanietz, M. G., *FASEB J.* 13, 1658-1676 (1999). This possibility is less likely, because binding of phorbol ester to DGKδ in vitro has not successfully detected.

DGKδ, a type II DGK, has an important role in mammalian development. Ding et al., reported that DGKζ, a type IV DGK, had temporally and spatially restricted expression during mouse development. Ding, L., et al., *FEBS Lett.* 429, 109-114 (1998). DGKζ was highly expressed in neuronal structures, especially those involved in sensory input. Though its role in development of these structures is unclear, Topham et al. showed that DGKζ contributed to cell cycle control by regulating fluctuations of nuclear diacylglycerol. Topham, M. K., et al., *Nature*394, 697-700 (1998). Unlike DGKδ, DGKζ activity inhibited cell proliferation. Thus, DGKs have distinct roles in development of several organ systems, and the effects of their activity can either enhance or attenuate cell proliferation. In future studies, it will be important to investigate whether the expression and activity of DGKδ is abnormal in cancer, Alzheimer's disease and inflammation DGKδ may provide a key target for drug development for these diseases.

The method of the present invention can be used to screen for agents that regulate TACE activity, regulate the shedding and activity of TGFα or other proteins which are shed by TACE, regulate cell growth and division, and reduce inflamation. Such regulatory agents may either increase or decrease the level of DGKδ activity in a cell or organism thereby regulating TACE, TGFα, cell growth, and inflamation. To determine if a test agent has such regulatory properties a cell may be contacted with a test agent. Such cells can be any cell line that has at least one copy of a DKGδ gene and that expresses a level of the DGKδ gene product. However, it may be advantageous to use a cell line that overexpresses DGKδ so that levels of DGKδ and its function may be more readily determined. The level of DGKδ expression or function in the cell contacted with the test agent can be compared to the level in a control cell that has not been contacted by the test agent. Agents that increase or decrease the level of DGKδ have potential for regulating TACE activity, regulating the shedding and activity of TGFα or other proteins which are shed by TACE, regulating cell growth and division, and reducing inflamation.

The determination of the level of DGKδ in the cell may be determined by a variety of methods known in the art. For example one could detect the amount off DAG to conversion PA. Immunoblot detection or other direct detection methods could be used to determine the amount of DKGδ expressed in the cell. DGKδ mRNA levels may also be used to determine whether an agent affects the function of DGKδ in the cell.

Compounds that inhibit or increase DGKδ activity may act by various mechanisms. For example, a compound may inhibit or enhance DGKδ's enzymatic conversion of DAG to PA. Such inhibition of conversion may be accomplished by preventing the binding of DAG to DGKδ. Other agents may function by preventing the transcription of the DKGα gene or the translation of DGKδ mRNA. Such compounds may be for example, antisense nucleic acids or compounds which bind to nucleic acid molecules.

The cells used to determine the potential of the screen agents may be any of a number of types of cells known in the art. For example, the cell may be grown in a cell culture. Such cultured cells may be cancer cells, Hep G2 cells, hepatocytes, fibroblast, just to name a few. Additionally, the cell may be a cell within a multicellular organism. For example a mammal such as a mouse can be used. The cells or organism that are used to screen compounds according to the method of the invention can be naturally occuring cells and organism or can be engineered to produce higher a desired level of DGKδ. Additionally the cells or organisms may be engineered to express a transgenic DGKδ such as human DGKδ.

From such screening methods, methods of regulating the activity of TACE, the activity of TGFα or other proteins which are shed by TACT, cell growth and division, and inflamation may also be developed. The methods include the administering an effective amount of a compound that reduces or increases the activity DGKδ. The compound may be selected by the methods described herein which screen agents by measuring their potential to regulate DGKδ. Such compounds used in cell cultures or by administration to an animal.

All publications, patents, and patent applications cited herein are hereby incorporated by reference.

DEFINITIONS

As used herein, the term "cell line" or "cell culture" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "over-expression" as used herein denotes that a given gene product is being expressed in a cell or set of cells that have been engineered to express the gene product at a rate higher than in a comparable cell or set of cells that have not been so engineered. The rates of overexpression in said cells vary from the original levels by 2-fold, 5-fold, 10-fold or other rate of overexpression.

The term "suppressed" as used herein denotes that a given gene product is being present in a cell, a set of cells, or an animal at a rate lower than the normal wild type level. Suppression may occur from a naturally occurring or engineered mutation to the gene or by contacting the cell, set of cells, or the animal with a compound that is known to suppress the expression of the gene or inactivate the gene product. Suppression also refers to the state when none of a given gene product is present in the cell, cell line, or animal.

The term "inhibited" as used herein denotes that a given gene product, mRNA, or reaction is present in a cell or organism at a level lower than that of a control. Inhibition also refers to a state when none of the gene product, mRNA, or reaction is observed in the cell or organism.

As used herein, "effective amount" means an amount of a drug or pharmacologically active agent that is nontoxic but sufficient to provide the desired local or systemic effect and performance at a reasonable benefit/risk ratio attending any medical treatment.

In order to better describe the details of the present invention, the following discussion is divided into ten sections: (1) DGKδ is required for normal epithelial development in multiple organs; (2) Generation of DGKδ-deficient mice; (3) the DGKδ knockout phenotype is similar to TACE and EGFR mutant phenotypes; (4) targeted deletion of other DGKs do not have a similar phenotype to dgkd$^{-/-}$ mice; (5) downstream signaling by EGFR is not significantly altered in DGKδ knockout mice; (6) TGFα shedding from DGKδ knockout cells is significantly reduced; (7) overexpression of DGKδ in either COS7 or dgkd$^{-/-}$ cells activates TGFα shedding; (8) DGKδ and TACE interact in vivo; and (9) dysregulated activity of DGKδ affects cell growth and may lead to transformation.

DGKδ is Required for Normal Epithelial Development in Multiple Organs.

To elucidate the biologic function of DGKδ, mice were generated with a targeted mutation of the DGKδ gene. Unexpectedly, DGKδ mutant mice had a phenotype very similar to that of mice deficient in the tumor necrosis factor-α converting enzyme (TACE/ADAM 17), a member of the ADAM (a disintegrin and metalloprotease) family of proteins. Black, R. et al. *Nature* 385, 729-733 (1997); Moss, M. L. et al. *Nature* 385, 733-736 (1997).

TACE is a widely-expressed, transmembrane protein that initially translated with an N-terminal prodomain that is subsequently removed to generate a catalytically active metalloproteinase. Black, R. et al. *Nature* 385, 729-733 (1997); Moss, M. L. et al. *Nature* 385, 733-736 (1997). Its extracellular portion contains a zinc-dependent, catalytic motif and a cysteine-rich domain composed of disintegrin and "epidermal growth factor-like" regions. These motifs are followed by a transmembrane domain and a cytoplasmic tail. The specific function of the cytoplasmic tail is not clear. In fact, an alternatively spliced TACE mRNA that lacks the entire cytoplasmic tail has been isolated and its protein product still sheds a subset of TACE substrates. Reddy, P. et al. *J. Biol. Chem.* 275, 14608-14614 (2000). TACE was originally identified by its ability to proteolytically shed tumor necrosis factor-α (TNFα) from cells, process known as "ectodomain shedding." Black, R. et al. *Nature* 385, 729-733 (1997); Moss, M. L. et al. *Nature* 385, 733-736 (1997). Later studies indicated that TACE also cleaves several other biologically active proteins that are initially produced as membrane-bound precursor proteins. These include transforming growth factor-α (TGFα), β-amyloid precursor protein (β-APP), and L-selectin. Reddy, P. et al. *J. Biol. Chem.* 275, 14608-14614 (2000). More recent reports indicate that TACE may also shed growth hormone binding proteins, erbB4/HER4, and macrophage colony stimulating factor. Zhang, Y., et al. *Endocrinology* 141, 4342-4348 (2000); Rio, C., et al. *J. Biol. Chem.* 275, 10379-10387 (2000); Rovida, E., et al. *J. Immunol.* 166, 1583-1589 (2001). By virtue of its array of substrates, TACE is involved in diverse processes that are critical for the development and maintenance of mammalian organisms. For example, like DGKδ, targeted deletion of TACE is lethal due primarily to defects in maturation and organization of epithelial cells. Peschon, J. J. et al. *Science* 282, 1281-1284 (1998). Most of the defects in the TACE-deficient mice were similar those found in mice null for the epidermal growth factor receptor (EGFR). Miettinen, P. J. et al. *Nature* 376, 337-341 (1995). This was not surprising, since EGFR ligands are released from the cell surface by proteolytic cleavage, so these data indicate that TACE may have a significant role in releasing ligands that activate the EGFR. Dong, J. et al. *Proc. Natl. Acad. Sci. USA* 96, 6235-6240 (1999). In fact, murine fibroblasts null for TACE shed very little TGFα, indicating that TACE is predominantly responsible for proteolytic release of TGFα from cells. Peschon, J. J. et al. *Science* 282, 1281-1284 (1998). Because mice with targeted deletion of TGFα have a very mild phenotype compared to TACE- or EGFR-deficient mice, it is likely that in addition to TGFα, TACE sheds other EGFR ligands from cells. Mann, G. B. et al. *Cell* 73, 249-261 (1993).

Deregulated shedding of TGFα caused by abnormally high TACE activity could result in malignant transformation. Indeed, TGFα transgenic animals have several neoplastic lesions depending on the strain of mouse and the promoter regulating expression of TGFα Mann, G. B. et al. *Cell* 73, 249-261 (1993). And many cell lines can be transformed by overexpressing TGFα. Prenzel, N., et al. *Endocrine-Related Cancer* 8, 11-31 (2001). Shedding of TGFα appears to be an important component in this process, as mice expressing a TGFα transgene that could not be shed had a mild phenotype compared to mice expressing a TGFα transgene that could be shed. Sandgren, E. P., et al. *Cell* 61, 1121-1135 (1990). Thus, shedding of TGFα must be carefully regulated. Since TACE appears to be predominantly responsible for its release from cells, it follows that the activity of TACE must be precisely controlled. Supporting this, there are several examples of autocrine growth circuits dependent on TGFα, and in many cases, these circuits can be interrupted by metalloproteinase inhibitors, which attenuate TACE activity. Dong, J. et al. *Proc. Natl. Acad. Sci. USA* 96, 6235-6240 (1999).; Normanno, N., et al. *Front. Bioscience* 6, 685-707 (2001). These data suggest that some of these autocrine growth circuits are due to or dependent on TACE activity. Thus, careful regulation of TACE activity is critical, and its dysregulation—either too much or too little activity—can be deleterious.

It is known that upregulated cell surface TACE activity does not require TACE transcription, translation, or mobilization to the cell surface, suggesting that either TACE enzymatic activity is directly affected, perhaps by a conformational change, or that TACE substrates become more easily accessible. Peschon, J. J. et al. *Science* 282, 1281-1284 (1998); Doedens, J. R. & Black, R. A. *J. Biol. Chem.* 275, 14598-14607 (2000). Only a few factors that induce TACE-mediated shedding have been described. These include the phorbol esters, which are diacylglycerol analogues that, unlike DAG, are very slowly metabolized. Phorbol esters are primarily considered activators of PKCs, but they can also bind and activate other proteins. Ron, D. & Kazanietz, M. G. *FASEB J* 13, 1658-1676 (1999). Additionally, agonists that activate G protein-coupled receptors (GPCR), calcium ionophores, and unidentified serum factors also increase the proteolytic release of TACE products. Peschon, J. J. et al. *Science* 282, 1281-1284 (1998); Prenzel, N., et al. *Endocrine-Related Cancer* 8, 11-31 (2001). Although demonstrating that a variety of stimuli can activate TACE, these data, unfortunately, do not point to a clear model for TACE regulation. They suggest, however, that DAG signaling is important. For example, GPCRs activate PLC-β isozymes, which initiate DAG and calcium signaling, suggesting that DAG signaling is an important event leading to activation of TACE. This is consistent with its activation by phorbol esters, which are DAG analogues. These data also indicate that DAG is an activator in the cascade leading to TACE-mediated ectodomain shedding. If true, it is not clear the role that DGKδ—an enzyme traditionally thought to terminate DAG signaling—has in shedding, but based on the data that follows, it appears that DGKδ is an essential component in this process.

C. Preliminary Studies

Generation of DGKδ-Deficient Mice.

To generate a DGKδ null mutation, a targeted deletion was made of the N-terminal portion of DGKδ's catalytic domain (FIG. 1A-B), which is essential for its DAG kinase activity. Sakane, F., et al. *J Biol Chem* 271, 8394-8401 (1996). Heterozygous mice were viable and fertile and were intercrossed to obtain DGKδ-deficient (dgkd$^{-/-}$) mice. The genotype of the mice was determined by Southern analysis of tail DNA—with integration of the targeting vector, a 3.8 kb product instead of a 7.2 kb product was generated following EcoRI digestion (FIG. 1B-C). Further analysis indicated that the only integrated copy of the vector was at the target locus (data not shown). To examine expression of the DGKδ gene in wild-type and mutant mice, total RNAs was isolated from primary embryonic fibroblasts, reverse transcribed, and then primers corresponding to the 3' end of exon 4 and the 5' end of exon 9 were used to generate PCR products. Wild-type and, to a lesser extent, heterozygous RNAs directed the synthesis of the expected 0.57 kb reverse transcription (RT)-PCR product (FIG. 1D). There were no detectable bands using RNA from dgkd$^{-/-}$ mice, demonstrating that homozygous mutant mice express no normal or alternatively spliced DGKδ mRNA. To further confirm DGKδ gene in activation, antibodies directed against the C-terminus of DGKδ were used to immunoblot cell lysates of wild-type, heterozygous, and homozygous mutant embryonic fibroblasts. The expected 140 kDa band was observed in lysates from wild-type and heterozygous cells, but no 140 kDa protein was detected in lysates from the knockout mutation cells (FIG. 1E). Moreover, no smaller DGKδ protein products were found in the mutant cells, confirming the RT-PCR experiment. These data indicate that the DGKδ gene was successfully interrupted by targeted deletion.

The DGKδ Knockout Phenotype is Similar to TACE and EGFR Mutant Phenotypes.

Figure 2:
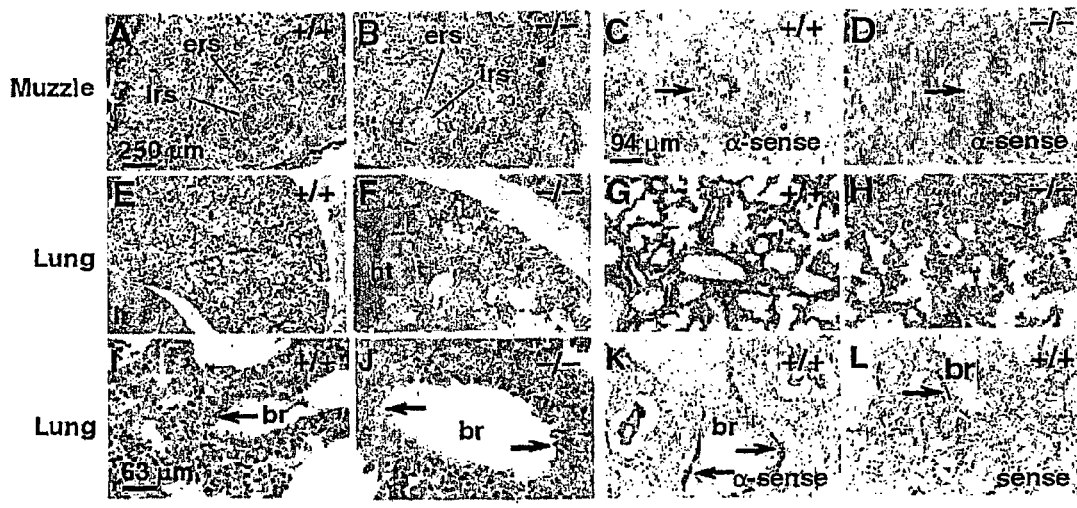
FIG. 2A is a photograph of a muzzle section from a wild-type mouse.
FIG. 2B is a photograph of a muzzle section from a dgkd$^{-/-}$ mouse.
FIG. 2C is a photograph of a muzzle section from a wild-type mouse.
FIG. 2D is a photograph of a muzzle section from a dgkd$^{-/-}$ mouse.
FIG. 2E is a photograph of a lung section of a wild-type mouse.
FIG. 2F is a photograph of a lung section from a dgkd$^{-/-}$ mouse.
FIG. 2G is a photograph of a lung section of a wild-type mouse.
FIG. 2H is a photograph of a lung section from a dgkd$^{-/-}$ mouse.
FIG. 2I is a photograph of a lung section of a wild-type mouse.
FIG. 2J is a photograph of a lung section from a dgkd$^{-/-}$ mouse.
FIG. 2K is a photograph of a lung section of a wild-type mouse.
FIG. 2L is a photograph of a lung section of a wild-type mouse.

At birth, the genotypes of progeny from dgkd$^{+/-}$ intercrosses were consistent with Mendelian patterns of inheritance, indicating that homozygous animals were not subject to prenatal lethality. Still, the homozygous dgkd$^{-/-}$ defect was invariably lethal; mutant mice died within 24 h after birth. Newborn dgkd$^{-/-}$ mice were identifiable by their open eyelids and moderately stunted whiskers. Normally, eyelids fuse at about embryonic day 16.5 (E16.5) and do not open until about postnatal day 14 (P14). Peschon, J. J. et al. *Science* 282, 1281-1284 (1998). In contrast, at E17.5 all dgkd$^{-/-}$ fetuses had open eyelids. Most dgkd$^{-/-}$ fetuses were smaller than their wild-type and heterozygous litter mates: dgkd$^{-/-}$ newborn mice weighed 1.10±0.21 g(n=11) as compared to wild type 1.39±0.15 g(n=11) and heterozygous 1.44±0.15 g(n=16) mice. Histological examination of dgkd$^{-/-}$ fetuses on E17.5 and at birth (P0) revealed additional defects. Dysgenesis characterized by delayed or impaired epithelial cell maturation in multiple organs, including the hair follicles, lungs, small intestine and placenta was observed (FIG. 2). For example, relative to wild-type, mutant hair (whisker) follicles were less differentiated morphologically (FIG. 2A-B), and transverse sections of hair follicles in muzzle skin revealed weak staining of eosinophilic granules in the internal root sheath and moderate hypercellularity in the external root sheath in knockout mice relative to wild-type. Consistent with this, it was found by in situ hybridization with a DGKδ probe that in wild-type hair follicle sections, the DGKδ mRNA was mainly detectable at the inner area of internal root sheath (FIG. 2C). In the sections from dgkd$^{-/-}$ mice, no signal was detected in this region (FIG. 2D). These defects likely contributed to the rudimentary whiskers that were observed in the dgkd$^{-/-}$ mice. The lungs of E17.5 and newborn dgkd$^{-/-}$ fetuses (which had respired) appeared immature with poorly inflated areas and abnormal airway branching (FIGS. 2E-H). Lung sections from these mutants showed undifferentiated epithelium in the respiratory bronchioles and alveoli and an increased number of cells in the alveolar sacs (FIG. 2I-J). In in situ hybridizations of wild-type lung sections, DGKδ mRNA was detected mainly in the epithelial cells in the respiratory bronchioles and alveolar sacs (FIG. 2K-L), which was where dysmorphic development was observed in the null mice. Other defects in the dgkd$^{-/-}$ mice were observed which are consistent with widespread dysregulation of epithelial maturation and organization. For example, sections of the proximal small intestine from dgkd$^{-/-}$ E17.5 fetuses revealed blunted villi and hypercellular, pseudostratified mucosal epithelium (not shown). Together with the overall expression pattern, these observations suggest that DGKδ plays an important role in the proliferation and differentiation of the epithelial compartment of these organs.

It was noted that the defects associated with the dgkd$^{-/-}$ mutation were very similar to those of mice lacking TACE and EGFR, suggesting that DGKδ participates in regulating signaling cascades common to TACE and EGFR. Peschon, J. J. et al. *Science* 282, 1281-1284 (1998); Miettinen, P. J. et al. *Nature* 376, 337-341 (1995).

Targeted Deletion of other DGKs do not have a Similar Phenotype to DGKD$^{-/-}$ Mice.

In an effort to determine the function of other DGK isotypes, the murine genes encoding DGKε (dgke$^{-/-}$) and DGKι (dgki$^{-/-}$) were interrupted. Both dgke$^{-/-}$ and dgki$^{-/-}$ mice had normal epithelial development and normal life spans. DGKε null mice were resistant to electroconvulsive shock with shorter tonic seizures and faster recovery, suggesting that DGKε helps modulate neuronal signaling pathways linked to synaptic activity, neuronal plasticity, and epileptogenesis. Rodriquez de Turco, E. B. et al. *Proc. Natl. Acad. Sci. USA* 98, 4740-4745 (2001). Into adulthood, dgki$^{-/-}$ mice do not have defects characteristic of the dgkd$^{-/-}$ mice. Combined with previous observations, this data indicate that DGK isotypes have distinct functions. Thus, the phenotype of the dgkd$^{-/-}$ mice reflects a requirement for DGKδ rather than a broad requirement for DAG kinases.

Downstream Signaling by EGFR is not Significantly Altered in DGKδ Knockout Mice.

The phenotype of the dgkd$^{-/-}$ mice was consistent with several possibilities. The most likely of which included a requirement for DGKδ in activation of TACE or in downstream signaling from the EGFR. Another possibility was that deletion of DGKδ reduced expression of either EGFR or TACE. To assess whether the deletion affected their expression, the amount of each protein in cells from wild type, heterozygous and homozygous mutant mice was compared. By Western blotting, no difference was found in EGFR (FIG. 3) or TACE (not shown) expression between the cell lines, indicating that the deletion did not affect expression of either protein. Moreover, the ratios between premature, glycosylated and mature forms of TACE were indistinguishable in the three cell populations, indicating that expression of TACE and its post-translational modification was also normal in the knockout cells.

Figure 3:
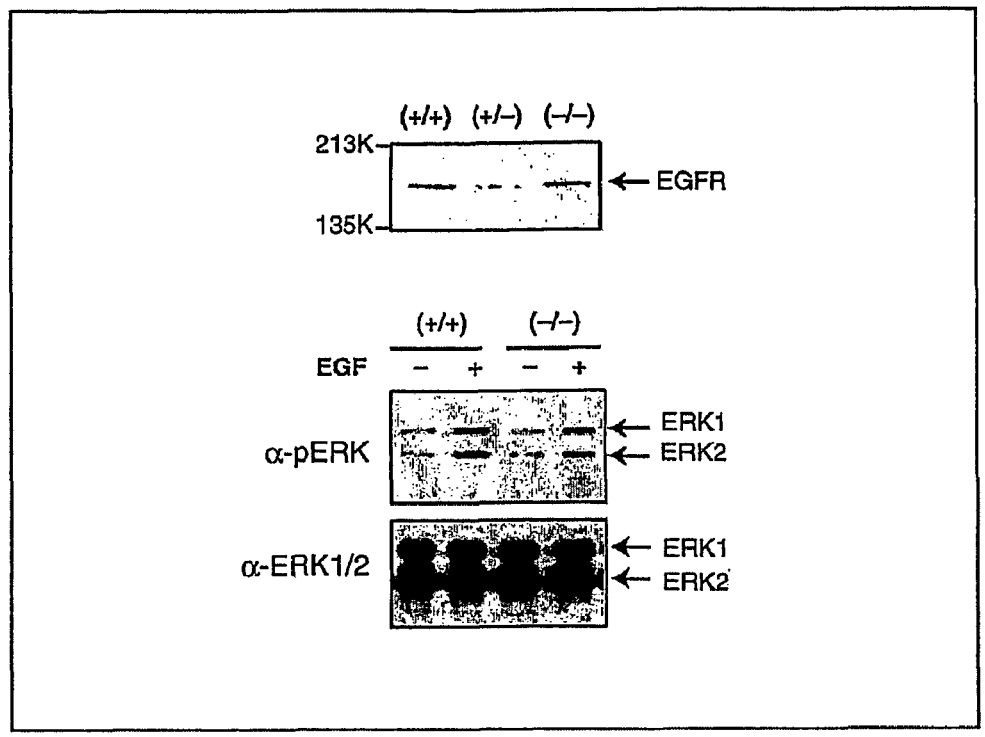
FIG. 3 is a set of photographs showing expression levels of EGFR and analyses of EGFR downstream signaling.

Whether signaling downstream of EGFR was affected in DGKδ mutant mice was also examined. Since the MAPK pathway is a major route of EGFR signaling, ERK phosphorylation was examined in cell lines developed from knockout mice. Prenzel, N., et al. *Endocrine-Related Cancer* 8, 11-31 (2001). In primary embryonic fibroblasts from wild-type mice, exogenous EGF caused a 2.2 fold increase in phosphorylated ERK1 and 2 as judged by densitometry of the immunoblot bands (FIG. 3). A comparable increase (2.1 fold) was detected in primary embryonic fibroblasts from DGKδ null mice. Control measurements showed that the concentrations of ERK1 and ERK2 (a mixture of phosphorylated and nonphosphorylated forms) in these two cell populations were indistinguishable. These results demonstrate that deletion of DGKδ did not affect MAPK activation downstream of EGFR. Activation of EGFR signaling is known to mediate stress fiber formation induced by serum factors. Prenzel, N., et al. *Endocrine-Related Cancer* 8, 11-31 (2001). To further confirm that DGKδ did not affect the EGFR signaling pathway, cell spreading on fibronectin was examined and no difference between mutant and wild-type embryonic fibroblasts was found (not shown). These results further support the conclusion that signaling downstream of EGFR is unchanged by deletion of DGKδ function. Thus, whether DGKδ affects the activity of TACE was examined next.

TGFα Shedding from DGKδ Knockout Cells is Significantly Reduced.

TACE was originally identified as the enzyme that proteolytically releases TNFα from the cell surface. Black, R. et al. *Nature* 385, 729-733 (1997); Moss, M. L. et al. *Nature* 385, 733-736 (1997). Whether deleting DGKδ affected ectodomain shedding of TNFα from liver and spleen cell suspensions was tested—where hematopoietic activity is highest in newborn mice. Tamura, K. et al. *Cell* 102, 221-231 (2000). To induce release on TNFα, the cell suspensions were stimulated with lipopolysaccharide (LPS, 5 μ/mL), PMA (50 ng/mL), or a combination of LPS (5 μg/mL) and PMA (50 ng/mL). As measured by ELISA, both agents induced release of TNFα into the medium, with LPS inducing a five-fold increase and PMA causing a three-fold increase. Combining LPS and PMA increased TNFα shedding twenty-fold. It was found that deletion of DGKδ did not affect release of TNFα from the cells (not shown), indicating that DGKδ does not have a regulatory role in its release. This did not rule out that DGKδ could affect TACE, because DGKδ is an intracellular protein, and Reddy et al found that the cytoplasmic tail of TACE was not necessary for stimulated shedding of TNFα. Reddy, P. et al. *J. Biol. Chem.* 275, 14608-14614 (2000)

Figure 4:
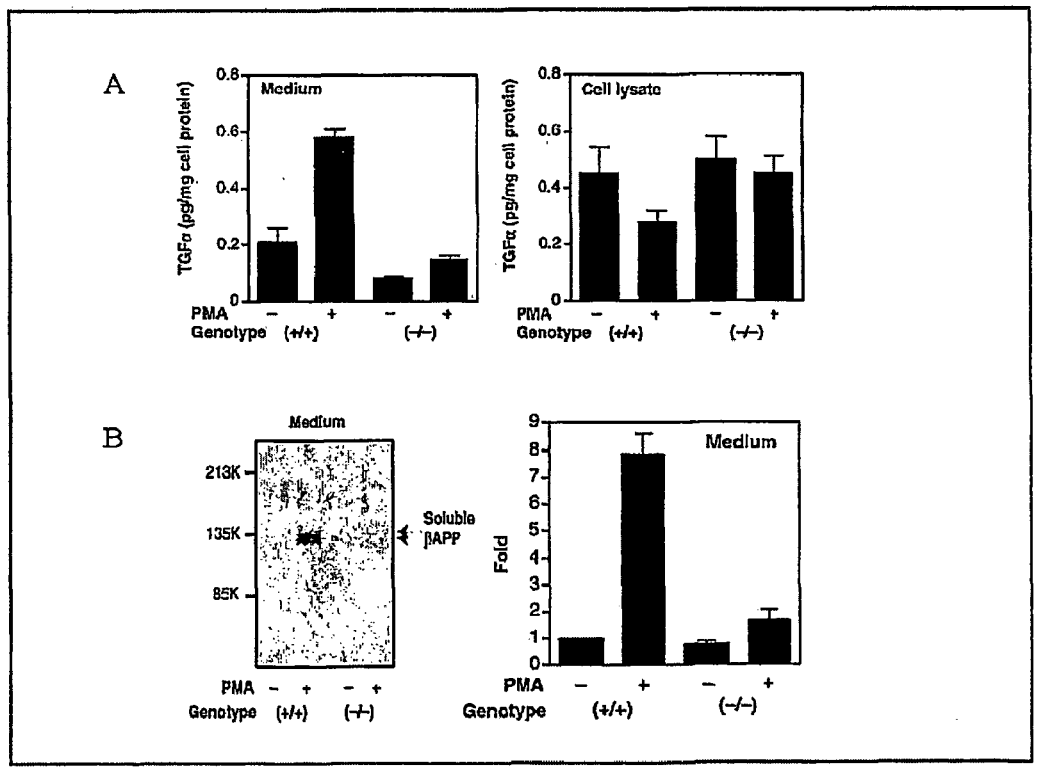
FIG. 4A is a set of graphs showing TACE activity in DGKδ-knockout embryonic fibroblasts.
FIG. 4B is a photograph and a graph showing TACE activity in DGKδ-knockout embryonic fibroblasts by illustrating the amount of secreted β-APP.

TACE is the only enzyme known to shed soluble TGFα, a process enhanced by stimulation with serum or PMA. Peschon, J. J. et al. *Science* 282, 1281-1284 (1998). It is not known whether or not the cytoplasmic tail of TACE is required to activate TGFα shedding. To test if DGKδ affected release of TGFα, the amounts of soluble TGFα in the culture media of dgkd$^{-/-}$ and wild-type embryonic fibroblasts transfected with pro-TGFα were compared. It was found that the amounts of cell-associated TGFα in mutant and wild-type cells were comparable (FIG. 3A, right), but that basal release of TGFα was two-fold higher in the wild-type cells (FIG. 4A, left), suggesting that DGKδ may regulate basal and perhaps stimulated TGFα shedding. Supporting a role for DGKδ in stimulated TGFα shedding, PMA-induced shedding of TGFα by dgkd$^{-/-}$ cells was approximately 25% that of stimulated wild-type cells (FIG. 4A, left). These data indicate that DGKδ has an important role in the proteolytic release of TGFα. Since TACE is the only enzyme known to shed TGFα, DGKδ was likely affecting TACE. TACE is also known to cleave β-APP, so the release of endogenous β-APP from embryonic fibroblasts was examined next. Reddy, P. et al. *J. Biol. Chem.* 275, 14608-14614 (2000). PMA caused a 6-8 fold increase in β-APP shedding from dgkd$^{+/+}$ cells, while it only induced a moderate increase in shedding of β-APP from dgkd$^{-/-}$ cells (FIG. 4B). The levels of endogenous cell-associated β-APP were identical in the two cell populations, as judged by immunoblotting whole cell lysates (not shown) indicating that deletion of DGKδ did not affect expression of β-APP. Taken together, these results strongly indicate that DGKδ positively regulates the activity of TACE toward a subset of its substrates and that a deficiency of DGKδ function significantly reduced TACE activity, which disrupted epithelial development in dgkd$^{-/-}$ mice.

Overexpression of DGKδ in either COS7 or dgkd$^{-/-}$ Cells Activates TGFα Shedding.

Figure 5:
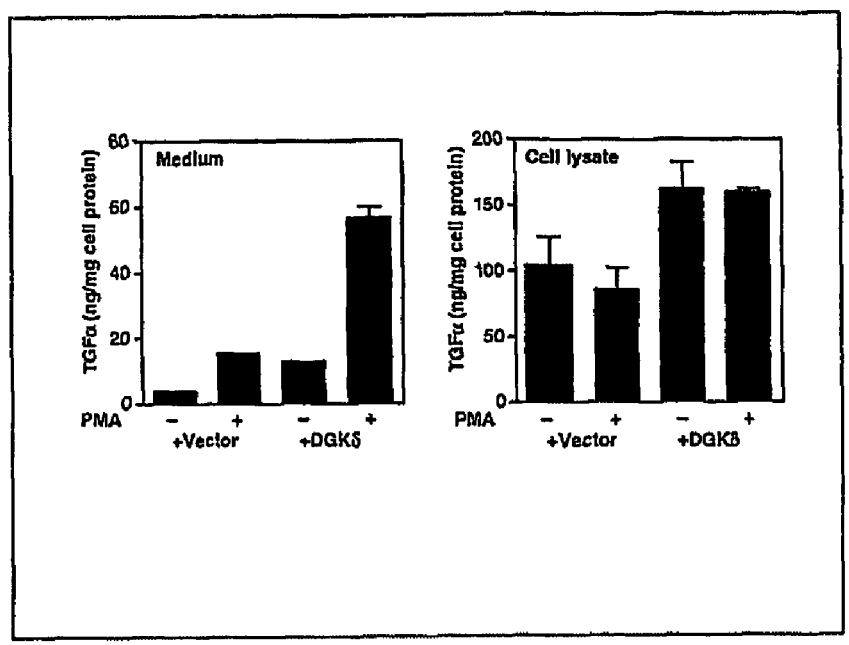
FIG. 5 is a set of bar graphs showing the overexpression of DGKδ augments TGFα shedding.

The previous experiments demonstrated that loss of DGKδ attenuated TGFα shedding from cells. To test whether overexpression of DGKδ, could activate TGFα shedding, DGKδ and pro-TGFα were co-transfected into COS7 cells and then the release of TGFα from the cells was measured. An increased basal TGFα shedding in cells overexpressing DGKδ was observed relative to control cells (FIG. 5, left). And following stimulation with PMA, cells overexpressing DGKδ showed an approximately 4-fold increase in TGFα release compared to control cells (FIG. 5, left). The amounts of cell-associated TGFα in control vector- and DGKδ-transfected cells were comparable (FIG. 5, right), and could not account for the difference in TGFα shedding. These results support the hypothesis that DGKδ regulates TGFα release, likely through an effect on TACE. Whether transient expression of DGKδ in dgkd$^{-/-}$ fibroblasts could restore TGFα shedding was also examined. Using dgkd$^{-/-}$ fibroblasts that compared to cells transfected with a control vector, it was found that transient expression of DGKδ doubled basal shedding of TGFα and tripled its release induced by 1 μM PMA (not shown). Thus, transient expression of DGKδ in dgkd$^{-/-}$ cells restored both basal and induced shedding of TGFα.

DGKδ and TACE Interact in vivo.

Figure 6:
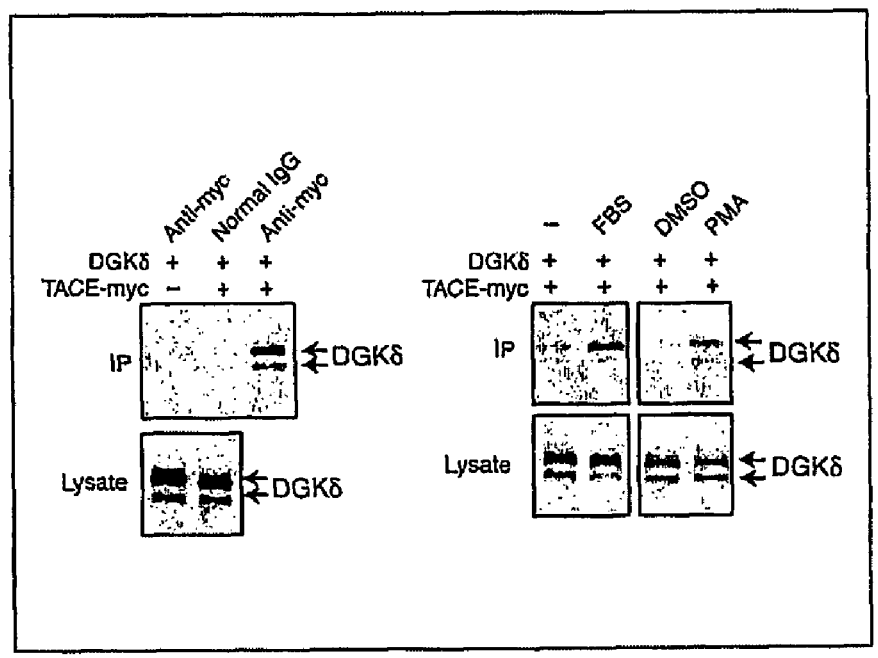
FIG. 6 is a set of photographs of immunoblots showing that the coimmunoprecipitation of DGKδ and TACE is augmented by factors that stimulate TACE activity.

According to previous experiments, DGKδ appears to regulate the activity of TACE toward some of its substrates. Based on the data, however, it is not clear whether DGKδ directly activates TACE or indirectly affects its activity through another protein. It was hypothesized that in order to regulate TACE, DGKδ must associate with it or a complex of proteins that contains TACE. To address whether this occurs in vivo, the enzymes were overexpressed in COS7 cells and then co-immunoprecipitation analysis was performed. Myc-tagged TACE in cell lysates was immunoprecipitated with an anti-myc monoclonal antibody, and then immune complexes were analyzed for co-immunoprecipitation of DGKδ by immunoblotting. When cells were grown in normal medium (10% FBS) DGKδ clearly co-immunoprecipitated with TACE (FIG. 6 left). Controls using normal IgG for immunoprecipitation instead of anti-myc antibody, or where anti-myc was used, but myc-TACE was not included in the transfection, established the specificity of DGKδ-TACE co-immunoprecipitation. Two agents previously shown to induce TACE activity are serum factors and PMA. Following starvation (0.5% serum for 2 hrs), it was found that the addition of either serum or PMA to the cells significantly increased co-immunoprecipitation of DGKδ and TACE (FIG. 6). Thus, stimuli that increase TACE activity enhance an interaction between DGKδ and TACE, providing further evidence that DGKδ positively regulates TACE activity.

Dysregulated Activity of DGKδ Affects Cell Growth and may Lead to Transformation.

Figure 7:
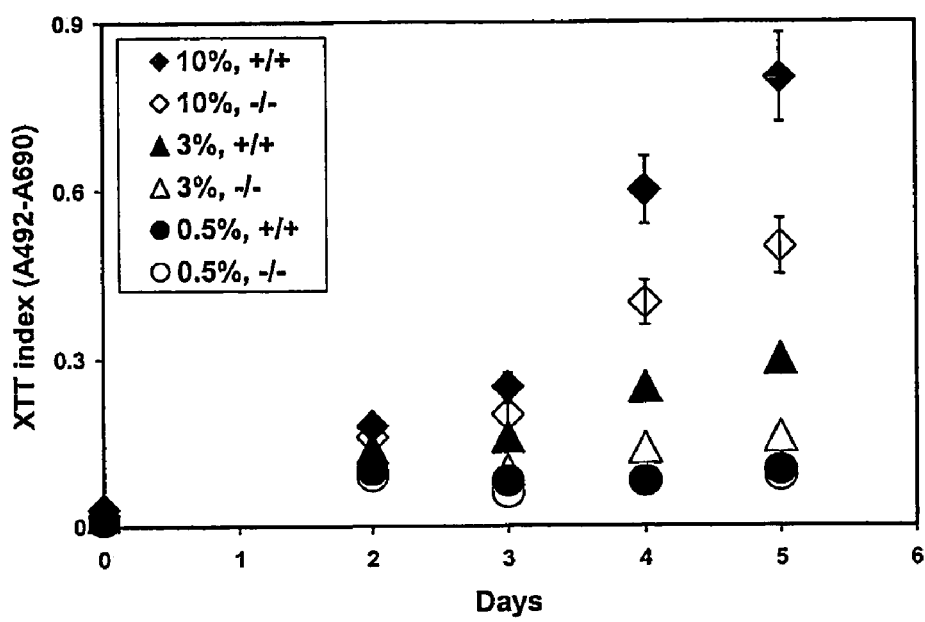
FIG. 7 is a graph showing that growth of dgkd$^{+/+}$ or dgkd$^{-/-}$ fibroblasts in 10%, 3%, or 0.5% serum.

TACE sheds TGFα and probably other growth factors that contribute to cell proliferation. Supporting this, Zhao et al noted that at embryonic day 16.5, epithelial proliferation in lungs from TACE deficient mice was significantly lower than in wild type mice (22.6% vs. 62.6%, p<0.05) Zhao, J. et al. *Dev. Biol.* 232, 204-218 (2001). Since DGKδ activates TACE, its loss may have the same effect. To examine this, the proliferation of DGKδ deficient murine embryonic fibroblasts (MEFs) was compared with wild type MEFs. It was found that dgkd$^{-/-}$ cells grew significantly more slowly when exposed to 3% or 10% serum than the wild type cells (FIG. 7). The difference in growth was not apparent in very low serum conditions, indicating that DGKδ regulates cell proliferation that is induced by serum factors.

As an activator of TACE, abnormally high activity of DGKδ may cause dysregulated shedding of TGFα or other growth factors, which may in turn induce uncontrolled cell proliferation through an autocrine stimulation loop. DGKδ is widely expressed, so its overexpression may contribute to transformation in many tissues. Since deletion of DGKδ caused dysmorphic epithelial development in the lungs of null mice, and TGFα may also cause dysregulated growth of lung carcinomas by autocrine stimulation, the overexpression of DGKδ mRNA was tested in several lung tumor cell lines. Normanno, N., et al. *Front. Bioscience* 6, 685-707 (2001). In these experiments, cDNA microarrays were used to assay for differences in expression of mRNA between cultured cells derived from several lung tumors and a cell line, CCD-13Lu, from normal lung. It was found that compared to the non-transformed lung cell line, CCD-13Lu, over 50% of cell lines derived from lung cancer tissue had significantly high overexpression of DGKδ mRNA (see Aim 3, Table 2). These data indicate that abnormally high DGKδ activity may contribute to malignant transformation of cells.

Figure 8:
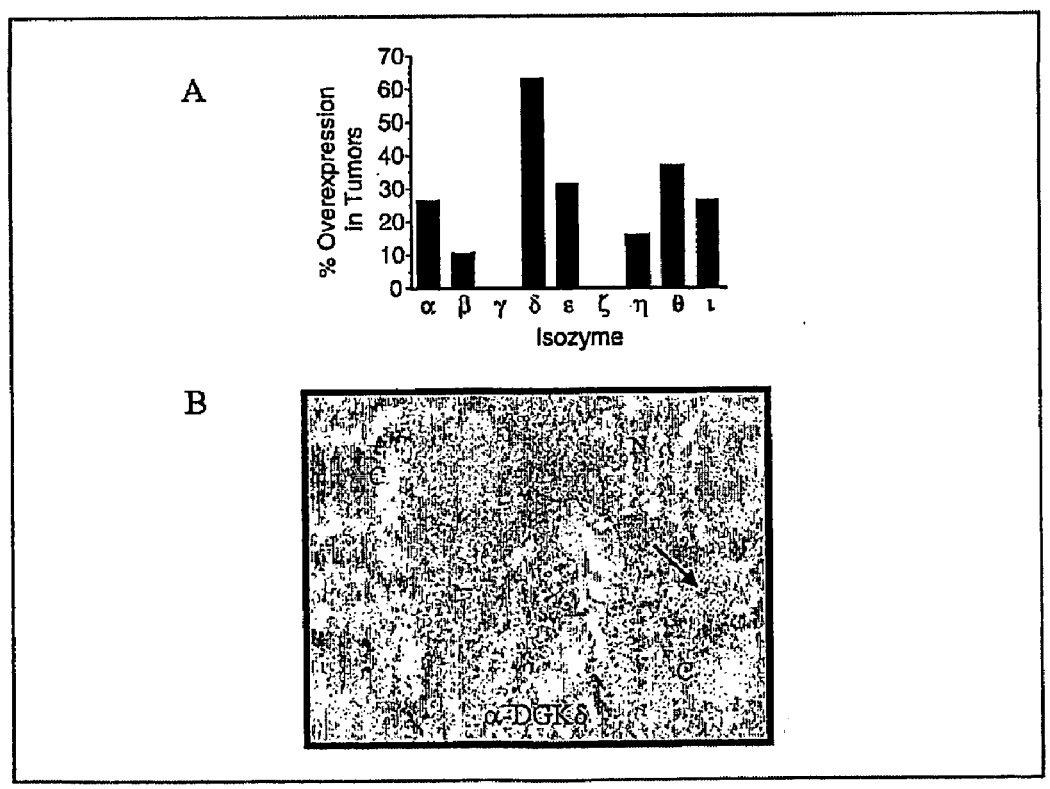
FIG. 8A is a bar graphs showing the DGKδ levels in normal and cancerous tissues.
FIG. 8B is a photograph showing immunohistochemical staining of DGKδ in liver tissue.

In past work, serum TGFα levels have been closely linked to the severity of hepatocellular carcinoma. Chung, Y. H. et al. *Cancer* 89, 977-982 (2000). Sakane et al have previously observed that a liver tumor cell line, HepG2, expressed high levels of DGKδ mRNA. Sakane, F., et al *J Biol Chem* 271, 8394-8401 (1996) So it was asked whether DGKδ mRNA was highly expressed in tissue from liver tumors. To determine this, the expression of DGKδ mRNA in hepatocellular carcinoma tissue specimens was assayed by RT-PCR and compared it to morphologically normal surrounding hepatic tissue. Significant overexpression of DGKδ mRNA was found in 63.2% of the samples (n=19). This degree of overexpression was at least double that of other known DGK isoforms (FIG. 8A), indicating that abnormally high overexpression of DGKδ may contribute to progression of hepatocellular carcinoma. To more directly assess if hepatic tumor tissue expresses more DGKδ than normal hepatic tissue, it was asked whether there were differences in protein expression of DGKδ in hepatocellular tumor tissue compared to normal surrounding tissue. The expression of DGKδ was examined by immunohistochemistry in nineteen formalin-fixed, paraffin-embedded hepatocellular carcinoma samples and found, in agreement with the RT-PCR data, that DGKδ was highly expressed in 79% of them. Surrounding, morphologically normal tissue expressed very little or no DGKδ (FIG. 8B). These data indicate that DGKδ can contribute to tumor development in lung, liver, and perhaps other tissues.

We claim:

1. A method of screening for agents that potentially regulate mammalian tumor necrosis factor-α converting enzyme (TACE) activity comprising:
    contacting a cell with a test agent, wherein the cell expresses or over-expresses mammalian diacylglycerol kinases delta (DGKδ); and
    measuring the level of DGKδ activity in the cell, wherein a test agent which increases or decreases the activity of mammalian DGKδ in the cell is a potential agent for regulating mammalian TACE activity.

2. The method of claim 1, where the activity of DGKδ is enzymatic conversion of diacylglycerol (DAG) to phosphatidic acid (PA).

3. The method of claim 2, wherein the test agent interferes with binding of DAG to DGKδ.

4. The method of claim 1, wherein the cell is part of a multicellular organism.

5. The method of claim 1, wherein the cell is selected from the group consisting of a lung cell, a HepG2 cell, a fibroblast, and a hepatocyte.

6. The method of claim 1, wherein the TACE activity is proteolytic release of transforming growth factor-α (TGFα).

7. The method of claim 1, wherein the TACE activity is the proteolytic release of a membrane bound protein.

8. The method of claim 7, wherein the membrane bound protein is selected from the group consisting of tumor necrosis factor-α (TNFα), transforming growth factor-α (TGFα), β-amyloid precursor protein (β-APP), L-selectin, p75 TNF receptor, p55 TNF receptor, growth hormone binding protein, erbB4/Her4, interleukin-6 receptor alpha, notch receptor, EGF, amphiregulin, betacellulin, epiregulin, heparin binding EGF (HB-EGF), and epigen.

9. A method of screening for agents that potentially regulate mammalian tumor necrosis factor-α converting enzyme (TACE) activity comprising:
    contacting a cell with a test agent, wherein the cell expresses or over-expresses a mammalian diacyiglycerol kinases delta (DGKδ) gene product; and
    measuring level of the mammalian DGKδ gene product or mammalian DGKδ mRNA expressed in the cell, wherein a test agent which reduces or increases the level of the mammalian DGKδ gene product or mammalian DGKδ mRNA is a potential agent for regulating mammalian TACE activity.

10. The method of claim 9, wherein the cell is selected from the group consisting of a cancer cell, a HepG2 cell, a fibroblast, and a hepatocyte.

11. The method of claim 9, wherein the cell is part of a multicellular organism.

12. The method of claim 9, wherein the TACE activity is proteolytic release of transforming growth factor-α (TGFα).

13. The method of claim 9, wherein the TACE activity is the proteolytic release of a membrane bound protein.

14. The method of claim 13, wherein the membrane bound protein is selected from the group consisting of tumor necrosis factor-α (TNFα), transforming growth factor-α (TGFα), β-amyloid precursor protein (β-APP), L-selectin, p75 TNF receptor, p55 TNF receptor, growth hormone binding protein, erbB4/Her4, interleukin-6 receptor alpha, notch receptor, EGF, amphiregulin, betacellulin, epiregulin, heparin binding EGF (FIB-EGF), and epigen.

* * * * *

UNITED STATES PATENT AND TRADEMARK OFFICE
CERTIFICATE OF CORRECTION

PATENT NO.         : 7,241,570 B2
APPLICATION NO. : 10/471122
DATED               : July 10, 2007
INVENTOR(S)       : Stephen Prescott et al.

It is certified that error appears in the above-identified patent and that said Letters Patent is hereby corrected as shown below:

In column 4, line 48, please replace "the cell maybe grown" with --the cell may be grown--.

In column 4, line 49, please replace "cultured cells maybe cancer cells" with --cultured cells may be cancer cells--.

In column 7, line 26, please replace "In vitro experiment shave indicated" with --In vitro experiments have indicated--.

Signed and Sealed this

Twenty-fifth Day of September, 2007

JON W. DUDAS
*Director of the United States Patent and Trademark Office*